US012740994B2

(12) United States Patent
Looijesteijn et al.

(10) Patent No.: US 12,740,994 B2
(45) Date of Patent: Sep. 22, 2026

(54) NUTRITIONAL COMPOSITION FOR STIMULATING BIFIDOBACTERIA

(71) Applicant: FrieslandCampina Nederland B.V., Amersfoort (NL)

(72) Inventors: Petronella Johanna Looijesteijn, Wageningen (NL); Cécile Marguerite Singh-Povel, Wageningen (NL); Arjen Nauta, Wageningen (NL)

(73) Assignee: FrieslandCampina Nederland B.V., Amersfoort (NL)

( * ) Notice: Subject to any disclaimer, the term of this patent is extended or adjusted under 35 U.S.C. 154(b) by 409 days.

(21) Appl. No.: 18/286,505

(22) PCT Filed: Apr. 12, 2022

(86) PCT No.: PCT/EP2022/059706

§ 371 (c)(1),
(2) Date: Oct. 11, 2023

(87) PCT Pub. No.: WO2022/218960

PCT Pub. Date: Oct. 20, 2022

(65) Prior Publication Data

US 2024/0197762 A1 Jun. 20, 2024

(30) Foreign Application Priority Data

Apr. 13, 2021 (EP) .................................... 21168007

(51) Int. Cl.

| | |
|---|---|
| ***A61K 31/702*** | (2006.01) |
| ***A23L 33/125*** | (2016.01) |
| ***A61P 1/00*** | (2006.01) |

(52) U.S. Cl.
CPC .......... *A61K 31/702* (2013.01); *A23L 33/125* (2016.08); *A61P 1/00* (2018.01)

(58) Field of Classification Search
None
See application file for complete search history.

(56) References Cited

U.S. PATENT DOCUMENTS

2012/0171165 A1 7/2012 Buck

FOREIGN PATENT DOCUMENTS

| | | |
|---|---|---|
| JP | 2021504421 | 2/2021 |
| WO | 2011008086 | 1/2011 |
| WO | 2017046711 | 3/2017 |
| WO | 2017144062 | 8/2017 |
| WO | 2018157900 | 9/2018 |
| WO | 2019106618 | 6/2019 |
| WO | 2020239724 | 12/2020 |

OTHER PUBLICATIONS

Arboleya, Silvia, et al.; "Gut Bifidobacteria Populations in Human Health and Aging", Frontiers in Microbiology, Aug. 2016, vol. 7, Article 1204 pp. 1-9.
International Search Report and Written Opinion, date of mailing Aug. 4, 2022, International Application No. PCT/EP2022/059706 (10 pgs.).
Leahy, S.C., et al.; "Getting better with bifidobacteria", Journal of Applied Microbiology, Jan. 2005, vol. 98, pp. 1303-1315.
Turroni, Francesca, et al.; "Exploring the Diversity of the Bifidobacterial Population in the Human Intestinal Tract", Applied and Environmental Microbiology, Mar. 2009, vol. 75, No. 6, pp. 1534-1545.
Wong, Chyn Boon, et al.; "Insights into the reason of Human-Residential Bifidobacteria (HRB) being the natural inhabitants of the human gut and their potential health-promoting benefits", FEMS Microbiology Reviews, Apr. 2020, vol. 44, No. 3, pp. 369-385.

*Primary Examiner* — Patrick T Lewis
(74) *Attorney, Agent, or Firm* — Fitch, Even, Tabin & Flannery LLP

(57) ABSTRACT

Nutritional composition comprising galacto-oligosaccharide (GOS) and 2'-fucosyllactose (2'-FL) in a GOS:2'-FL weight ratio of 1:9-9:1 for use in increasing the relative abundance of bifidobacteria, preferably *Bifidobacterium adolescentis* and/or *Bifidobacterium longum* in the gastro-intestinal tract of a non-infant human subject.

19 Claims, 1 Drawing Sheet

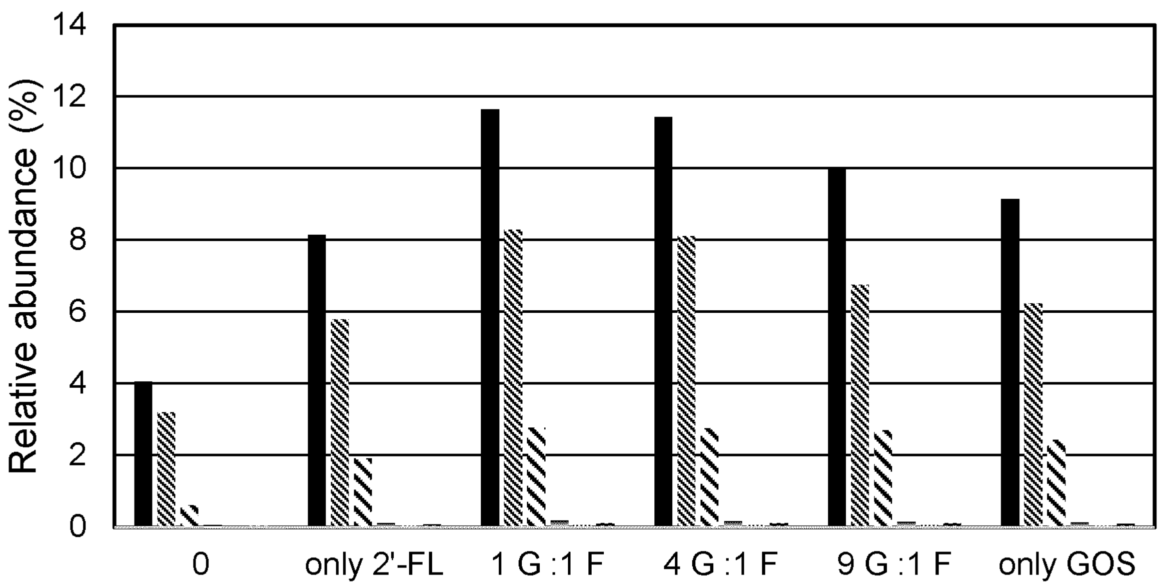
14
12
10
8
6
4
2
0
Relative abundance (%)
0
only 2'-FL
1 G :1 F
4 G :1 F
9 G :1 F
only GOS
Bifidobactera (total)
Bifidobacterium adolescentis
Bifidobacterium longum
Bifidobacterium catenulatum
Bifidobacterium breve
Bifidobacterium pseudocatenulatum

NUTRITIONAL COMPOSITION FOR STIMULATING BIFIDOBACTERIA

CROSS REFERENCE TO RELATED APPLICATIONS

This application is a U.S. national phase application of International Application No. PCT/EP2022/059706, filed Apr. 12, 2022, which claims benefit from European Application No. 21168007.9, filed Apr. 13, 2021, which are each hereby incorporated herein by reference in their entirety.

FIELD

The present invention relates to a nutritional composition for use in increasing the relative abundance of bifidobacteria in the gastro-intestinal tract of non-infant human subjects.

BACKGROUND

The food we consume dictates to a large extent the nature of the bacterial species in our gut microbiota. Various beneficial gut bacteria consume dietary fibres such a oligo- and polysaccharides. Human breast milk contains various oligosaccharides—classified as Human Milk Oligosaccharides (HMOs)—that are able to reach the intestinal tract undigested and unchanged. As a result, they can be utilized as primary carbon and energy source by specific gut microbiota components, in particular species of the genera *Bifidobacterium* and *Bacteroides*. These species have been shown to have beneficial impacts on infant health, more in particular in facilitating bacterial colonization in the gut and protection against pathogens.

BRIEF DESCRIPTION OF THE DRAWING

FIG. 1 displays the relative abundance bifidobacteria, relative to total bacteria content, obtained with different weight ratio's GOS and 2'-FL.

DETAILED DESCRIPTION

Although the amount and diversity of HMOs in human breast milk varies among women, e.g. depending on geographic origin and genetic background, it can be said that human breast milk contains three major HMO types: fucosylated HMOs (35%-50%), sialylated HMOs (12%-14%), and nonfucosylated neutral HMOs (42%-55%). Fucosylated HMOs include 2'-fucosyllactose (2'-FL), which is the most abundant HMO in human breast milk.

Bifidobacteria are common inhabitants of the human gut across our entire lifespan. They are saccharolytic organisms that have the ability to ferment glucose, galactose and fructose and are believed to play a pivotal role in maintaining a healthy gastrointestinal tract.

Bifidobacterial gut colonization starts at birth, and the process continuously progresses with the acquisition and loss of different species and strains over time. The transition from an infant microbiota towards an adult microbiota is believed to start after the dietary transition to solid food. One of the effects of this transition is a reduction in the relative abundance of bifidobacteria, from about 60-70% in infants to about 2-14% in adults.

Upon aging, the relative abundance of bifidobacteria tends to decline further, meaning that most elderly, e.g. above about 50, 60, or 70 years of age, have a significantly lower relative abundance of these species.

Colonisation by bifidobacteria is believed to play a vital role in maintaining human health. Various studies have shown that an increase in the abundance of bifidobacteria in the gastro-intestinal tract of non-infant human subjects is associated with prevention or treatment of enteropathogenic infections, type-2 diabetes, impaired gut-barrier function, gut brain disorders such as stress, anxiety, and depression, allergies such as atopic dermatitis, asthma, and inflammatory bowel conditions (WO 2018/157900, C. B. Wong et al., *FEMS Microbiology Reviews* 44 (2020) 369-385, and F. Turroni et al., *Applied and Environmental Microbiology* 75 (2009) 1534-1545)

More in particular, as disclosed by S. C. Leahy et al., *J. Appl. Microbiol.* 98 (2005) 1303-1315, with the decrease in bifidobacteria abundance in elderly, there is a corresponding increase in the number of less desirable microbial species and pathogenic organisms. Furthermore, bifidobacteria, in particular *B. longum*, have been shown to reduce the incidence and duration of antibiotic associated diarrhea and exhibit inhibitory effects on many other pathogenic organisms, such as *Salmonella typhimurium.*

In addition, a positive effect on constipation and a reduction of the gastrointestinal symptoms of severe premenstrual syndrome have been reported.

Different studies have focused on the relationship between the intestinal microbiota and the pathogenesis of irritable bowel syndrome (IBS), showing an altered microbiota related to IBS patients and lower levels in the *Bifidobacterium* genus. In the elderly gut microbiota, a reduction was observed in numbers of bifidobacteria in elderly people suffering from *Clostridium difficile*-associated diarrhea compared to a healthy control group. Decreased numbers of bifidobacterial have also been observed in other illnesses such as cystic fibrosis, hepatitis B and both diabetes Types I and II (S. Arboleya et al., Frontiers in Microbiology, 7 (2016) 1204).

Hence, there is a general desire to achieve an increase in bifidobacteria abundance in the gastro-intestinal tract of non-infant human subjects, more in particular adults, more in particular that of elderly persons.

A non-infant human subject in this document is defined as a human subject with an age of at least 3 years old.

Not only the number of bifidobacteria decreases with age, also the diversity of bifidobacteria species changes. *B. longum*, subspecies *longum* and *infantis, B. breve*, and *B. bifidum* are generally dominant in infants, whereas *B. catenulatum, B. adolescentis* and *B. longum* subspecies *longum* are more prevalent in adults (S. Arboleya et al., Frontiers in Microbiology, 7 (2016) 1204).

These different species display different abilities to consume various HMOs. The infant type bifidobacteria are adapted to utilise HMOs, while the majority of adult-type bifidobacteria are unable to utilise HMOs. *B. longum* subsp. *infantis* aggressively consumes almost all types of HMOs—including fucosylated and sialylated molecules—whereas the ability of *B. longum* subsp. *longum* strains to assimilate HMOs is limited. The majority of the *B. longum* subsp. *longum* strains were found to consume solely LNT and LNB, leaving other HMOs unmodified (C. B. Wong et al., FEMS Microbiology Reviews, 44, 2020, 369-385).

On the other hand, WO 2017/144062 and WO 2017/46711 disclose an increase in the relative abundance of *Bifidobacterium adolescentis* and *Bifidobacterium pseudocatenulatum* in the microbiota of the gastro-intestinal tract of non-infant humans by administering a neutral HMO, such as 2'-FL, and WO 2018/127900 discloses the administration for at least 14 days or less of a neutral HMO, such as 2'-FL, in order to increase the relative abundance of *Bifidobacterium longum* and/or *Bifidobacterium bifidum* in non-infant humans.

In other words, contradicting studies are available on the effect of HMO's, including 2'-FL, on the bifidobacteria in the non-infant microbiota, in particular the bifidobacteria abundance.

In our studies towards the effect of oligosaccharides on the bifidobacteria in the non-infant gut, it has now been surprisingly found that a combined administration of both GOS and 2'FL to non-infants, more in particular (elderly) adults, synergistically increases the relative abundance of bifidobacteria, in particular *Bifidobacterium adolescentis* and *Bifidobacterium longum* beyond the levels achieved by the individual administration of these compounds.

Although synergistic effects of these compounds on the infant microbiota have been suggested (WO2011/008086), a synergistic effect on the non-infant microbiota, in particular the bifidobacteria species, even more in particular the *Bifidobacterium adolescentis* and *Bifidobacterium longum* species in elderly adults, is surprising. As explained above, the gut flora of adults, compared to that of infants, is much more diverse, contains far less bifidobacteria, and also consists of different subspecies which are generally less responsive to 2'-FL.

The present invention therefore relates to the use of galacto-oligosaccharide (GOS) and 2'-fucosyllactose (2'-FL) in a GOS:2'-FL in a weight ratio of 1:9-9:1 for increasing the relative abundance of bifidobacteria, especially *Bifidobacterium adolescentis* and/or *Bifidobacterium longum* in the gastro intestinal tract of a non-infant human subject, preferably an adult human being, both therapeutically and non-therapeutically.

According to one embodiment, the present invention relates to a nutritional composition comprising galacto-oligosaccharide (GOS) and 2'-fucosyllactose (2'-FL) in a GOS:2'-FL weight ratio of 1:9-9:1 for use in increasing the relative abundance of bifidobacteria, preferably *Bifidobacterium adolescentis* and/or *Bifidobacterium longum* in the gastro intestinal tract of a non-infant human subject in a method for treating or preventing the development of a disease associated with a low relative abundance of bifidobacteria, preferably *Bifidobacterium adolescentis* and/or *Bifidobacterium longum.*

Examples of such diseases are enteropathogenic infections, impaired gut-barrier function, type-2 diabetes, gut brain disorders such as stress, anxiety, and depression, allergies such as atopic dermatitis, asthma, and/or inflammatory bowel conditions, such as inflammatory bowel disease (IBD). Inflammatory bowel disease (IBD) includes Crohn's disease (CD) and ulcerative colitis (UC).

The term "treatment", in relation a given disease or disorder, includes, but is not limited to, inhibiting the disease or disorder (e.g. arresting the development of the disease or disorder), relieving the disease or disorder (e.g. causing regression of the disease or disorder); and/or relieving a condition caused by or resulting from the disease or disorder (e.g. relieving, preventing or treating symptoms of the disease or disorder). The term "prevention" in relation to a given disease or disorder means preventing the onset of disease development if none has yet occurred, preventing the disease or disorder from occurring in a subject that may be predisposed to the disorder or disease but has not yet been diagnosed as having the disorder or disease, and/or preventing further disease/disorder development if already present.

In one embodiment, the nutritional composition is administered to a non-infant human subject having a lower than average abundance of bifidobacteria, preferably *Bifidobacterium adolescentis* and/or *Bifidobacterium longum* in the gastro intestinal tract and/or suffering from or being at risk of developing enteropathogenic infections, impaired gut-barrier function, type-2 diabetes, gut brain disorders such as stress, anxiety, and depression, allergies such as atopic dermatitis, asthma, and/or inflammatory bowel conditions, such as inflammatory bowel disease (IBD).

According to another embodiment, the invention relates to the non-therapeutic use of a nutritional composition comprising galacto-oligosaccharide (GOS) and 2'-Fucosyllactose (2'-FL) in a GOS:2'-FL weight ratio of 1:9-9:1 for increasing the relative abundance of bifidobacteria, preferably *Bifidobacterium adolescentis* and/or *Bifidobacterium longum* in the gastro intestinal tract of a non-infant human subject.

An increase in the relative abundance of bifidobacteria, preferably *Bifidobacterium adolescentis* and/or *Bifidobacterium longum* in the gastro intestinal tract of a subject as used herein refers to a higher number of these microorganisms relative to the total number of bacteria in the gastrointestinal tract of the subject after an intervention with the nutritional composition, as compared to prior to the intervention. The increase preferably is at least 3%, more preferably at least 8%, such as at least 10%, even more preferably at least 15%. The magnitude of the increase may depend on daily dosage of the nutritional composition. The relative abundance of these microorganisms may be determined as described below in the example.

A lower than average relative abundance of these microorganisms in the gastro intestinal tract as used herein refers to a lower number of these microorganisms relative to the total number of bacteria in the gastro intestinal tract of a subject as compared to the average number of these microorganisms intestinal tract of a group of 10 healthy subjects of the same age group. A healthy subject is a subject that has not been diagnosed with a disease and is not suffering from any problems relating to the gastro-intestinal tract.

The nutritional composition can be administered to any non-infant human subject, but is preferably administered to an adult human subject over 18, preferably over 40, more preferably over 50, even more preferably over 60, more preferably over 65 years of age, and most preferably at least 70 years of age.

The basic structure of galacto-oligosaccharide (GOS) includes a lactose core at the reducing end which is elongated with up to about seven galactose residues (degree of polymerization of 8; DP8). Commercial GOS preparations are generally produced via a transgalactosylation reaction by enzymatic treatment of lactose with β-galactosidase enzymes (EC.3.2.1.23), yielding a mixture of oligomers with approximately 100 different types structures with varying DP and linkages. Beta-galactosidase is produced in many microorganisms such as *Bacillus circulans*, *Aspergillus oryzae*, *Kluyveromyces marxianus*, *Kluyveromyces fragilis*, *Sporobolomyces singularis*, *Lactobacillus fermentum*, and *Papiliotrema terrestris* (*Cryptococcus Papiliotrema terrestris*). Beta-galactosidases differ in their three-dimensional structures, resulting in stereo- and regioselective formation of the glycosidic bonds.

After the enzymatic reaction, GOS is isolated and purified using conventional methods, such as nanofiltration and/or sequential simulated moving bed (SSMB). The resulting product is a GOS-containing syrup, which can be dried (e.g. by spray-drying, freeze-drying, or spray-cooling) to form a powder if so desired.

Particularly preferred types of GOS are GOS prepared by a beta-galactosidase enzyme originating from *Bacillus circulans*, such as Biotis™ GOS. Beta-galactosidase originating from *B. circulans* possesses particularly strong transgalactosylation activity and is commercialized worldwide.

The nutritional composition contains GOS and 2'-FL in a GOS:2'-FL weight ratio of 1:9-9:1, preferably in the range 1:8-8:1, more preferably 1:7-7:1, even more preferably 1:6-6:1, even more preferably 1:5-5:1, more preferably 1:4-4:1, more preferably 1:3-4:1, more preferably 1:2-4:1, most preferably 1:1-4:1.

The nutritional composition is preferably administered in a daily dosage of GOS plus 2'-FL of 0.5-30 g, preferably 0.5-20 g, more preferably 1-10 g, even more preferably 1-8 g, most preferably 2-6 g.

In this respect, it should be noted that GOS is a complex mixture of carbohydrates with differing chain length, linkage type, and degree of branching. It preferably comprises 40-100 wt %, more preferably 50-90 wt %, and most preferably 60-80 wt % oligosaccharides (DP≥3) on dry weight and may further contain monosaccharides like glucose and galactose, and disaccharides such as lactose, lactulose, and allolactose. The lactose content is generally in the range 0-60 wt %, preferably 0-40 wt %, and most preferably 0-30 wt %; the monosaccharide content is generally in the range 0-10 wt %; based on dry weight.

Any weight percentages of GOS in the present document are to be calculated based on the weight of di- and oligosaccharides (i.e. DP≥2) excluding lactose, present in said GOS. Lactose and monosaccharides, e.g. glucose and galactose, are, however, not included in the calculation.

The same holds for the weight ratios mentioned in the document: for their calculation, monosaccharides and lactose are not included but all longer sugars present in GOS (i.e. DP≥2), are taken into account.

In the nutritional composition according to the present invention, GOS and 2'-FL are preferably present in a total amount of at least 10 wt. %, e.g. at least 20 wt. %, at least 30 wt. %, at least 40 wt. %, at least 50 wt. %, at least 60 wt. %, at least 70 wt. %, at least 80 wt. %, or at least 90 wt. %, e.g. up to 91 wt %, 92 wt %, 93 wt %, or 94 wt %, relative to the total weight of the nutritional composition.

The nutritional composition can have the form of a food product, a beverage, or a dietary supplement. Furthermore, it may be administered as a prebiotic formulation i.e., without bacteria, or as a probiotic formulation i.e., with desirable (symbiotic) bacteria, such as Bifidobacteria and/or *Lactobacillus*.

The nutritional composition may have a liquid, semi-liquid, or solid constituency.

The food product is not milk of a mammal, such as not milk from a human, goat, sheep, cow, camel, ruminant. The food product or nutritional composition is a synthetic composition. The term “synthetic composition” designates a composition which is artificially prepared and preferably means a composition containing at least one compound that is produced ex vivo chemically and/or biologically, e.g. by means of chemical reaction, enzymatic reaction or recombinantly.

Examples of suitable food products and beverages are dairy products, such as milk, milkshake, chocolate milk, yoghurt, cream, cheese, pudding, and ice cream; bars, such as nutritional bars, energy bars, snack bars, cereal bars, and bars for diabetics; liquid products, such as nutritional drinks, diet drinks, liquid meal replacers, sports drinks, and other fortified beverages; savory snacks, such as chips, tortillas, puffed and baked snacks, crackers, pretzels, and savory biscuits; bakery products, such as muffins, cakes, and biscuits; sweets such as gummies and candies; and pastas, such as spaghetti.

Food supplements can have the form of pills, capsules, gummies, or dry powders. Food supplements may be ready for consumption or may need to be dissolved in a liquid like water. The product in dry powder form may be accompanied with a device, such as a spoon, to measure the desired amount of the powder (e.g. daily or unit dose). The nutritional composition may be provided in a jar, bottle, sachet, carton, rapping, and the like.

In a preferred embodiment, the nutritional composition is provided in the form of a single serving. Each single serving may optionally be individually packaged. A single serving preferably comprises 0.5-30 g, preferably 0.5-20 g, more preferably 1-10 g, even more preferably 1-8 g, most preferably 2-6 g 2'-FL and GOS.

Unit doses of the nutritional composition are preferably administered at least once a week, preferably at least once every 3 days, more preferably at least once every other day, most preferably at least once daily.

The treatment is preferably continued for a period of at least two weeks, e.g. at least 3 weeks, at least 4 weeks, at least 1 month, at least two months, at least three months, at least 4 months, at least 5 months, or even at least 6 months. In order to maintain the health benefits caused by the administration of the nutritional composition, said composition is preferably administered at least once per day. It may be taken together with a meal such as during breakfast or at the end of the day, e.g. 0-120 minutes, more preferably 0-60 minutes, and most preferably 0-30 minutes before going to bed. Alternatively, it may be administered twice per day, preferably in the morning and in the evening, e.g. during breakfast and dinner or during breakfast and before going to bed. Administration together with a meal is convenient, and lowers the risk that consumers forget to take the nutritional composition.

In a preferred embodiment, the nutritional composition further comprises other prebiotic components, such as fructo-oligosaccharides (FOS), inulin, and other HMOs. The nutritional composition may further contain lipids, digestible carbohydrates, proteins, and/or additional nutritional agents, such as vitamins, minerals, and/or biologically active peptides.

Examples of proteins are milk proteins (e.g. casein and/or whey protein), vegetable proteins (e.g. soy protein and/or rice protein), hydrolysates thereof, and mixtures thereof.

Examples of digestible carbohydrates are sucrose, lactose, glucose, fructose, corn syrup solids, starch, and maltodextrins.

Examples of vitamins and minerals are iron, magnesium, zinc, vitamin B3 and vitamin B6, vitamin D, vitamin C, vitamin E, and/or beta carotene.

The nutritional composition may further contain flavouring agents, preservatives and/or colouring agents.

EXAMPLES

Fecal Fermentations Simulating the Distal Colon of Elderly

Fecal fermentations were performed in a 24 well plate using the microMatrix™ (Applikon Biotechnology) as described in M. M. O'Donnell et al., Front. Microbiol., vol. 9, Aug. 10, 2018, article 1844. The wells were filled in the anaerobic chamber with medium (composition: see Table 1) to which the oligosaccharides GOS (Biotis™ GOS ex-FrieslandCampina), 2'-FL (Aequival™ 2'-FL, ex-FrieslandCampina), or mixtures thereof were added at a final concentration of 0 (blanc) or 0.5 wt % (every condition in duplicate). The plate was put in the microMatrix™ for about 20 minutes to reduce the dissolved oxygen concentration to below 5% and to increase the temperature of the medium to 37° C. After these 20 minutes, the plate was inoculated with a pool of fecal material of healthy 70+ human subjects and fermentations were started. During the fermentations, the pH of was controlled at pH 6.8 with a dead zone of 0.1 using ammonium gas and $CO_2$. The plates were orbitally shaken at 300 rpm. Mixed gas ($CO_2/H_2/N_2$: 10/5/85) was used to keep the cultures anaerobic during fermentation. After 7 hours of fermentation a sample of 1 ml was taken.

TABLE 1

Media composition (final concentration in well after addition of oligosaccharides and fecal pool):

| Component | g/L |
|---|---|
| Tryptone | 2 |
| Yeast extract | 2 |
| Cystein-HCl | 1 |
| Bile salts | 0.5 |
| $NaHCO_3$ | 2 |
| POE sorbitan monooleate (Tween ® 80) | 2 |
| Hemin | 0.05 |
| Vitamin K1 | 0.01 |
| NaCl | 0.1 |
| $KH_2PO_4$ | 0.04 |
| $K_2HPO_4$ | 0.04 |
| $CaCl_2 \cdot 6H_2O$ | 0.04 |
| $MgSO_4 \cdot 7H_2O$ | 0.01 |

Fecal Pool Preparation

Fecal samples of eight healthy elderly were included in the pool.

Inclusion criteria were: age >70 years; no intake of antibiotics, prebiotics, probiotics, and/or laxatives in the 3 months preceding donation; no symptoms of infection such as fever or diarrhea in the 3 days preceding donation; BMI between 22.5 and 27.5.

The individual fecal samples were 10 times diluted under anaerobic conditions by adding phosphate buffer (50 mM pH7.2±0.1, 0.05% Cysteine-HCl) and were homogenized with a stomacher. After that, 20% glycerol was added resulting in fecal slurries with a final fecal concentration of 8%. The fecal slurries were aliquoted and stored in the freezer (−80° C.). Just before inoculation of the plate, fecal samples of each of the eight donors were thawed and mixed in the anaerobic chamber. Each reactor well (working volume 5 ml) was inoculated with 625 μl fecal pool (1% feces).

Sample Preparation and Analysis

Immediately after inoculation, a sample of 1 ml was taken from wells without oligosaccharides. Furthermore, samples of 1 ml were taken (in the anaerobic chamber) during fermentation at t=7. The samples were centrifuged for 5 min at 13200 rpm at 4° C. The bacterial pellets were used for determination of microbiota composition using shotgun metagenomics sequencing (BaseClear) after DNA isolation (QIAamp PowerFecal Pro DNA kit). The supernatant was 10/100 times diluted with 30% acetonitrile and used for analysis of oligosaccharides by HPLC.

Results

As shown in FIG. 1, the relative abundance of both *B. adolescentis* and *B. longum* and their combined amount increased with the individual addition of 2'-FL and GOS compared to the blanc.

It can furthermore be observed that GOS has a stronger effect than 2'-FL. Surprisingly, however, when part of the GOS is replaced with 2'FL, the increase in relative abundance becomes even stronger, thereby evidencing a synergistic effect of 2'-FL and GOS.

The invention claimed is:

1. A method of treating or preventing the development of a disease associated with a low relative abundance of bifidobacteria in the gastro intestinal track of a non-infant human subject, wherein the non-infant human subject has a lower than average abundance of bifidobacteria in the gastro intestinal tract, the method comprising administering to the non-infant human subject an effective amount of a nutritional composition comprising galacto-oligosaccharide (GOS) and 2'-fucosyllactose (2'-FL) in a GOS:2'-FL weight ratio of 1:9-9:1.

2. The method of claim 1, wherein the disease associated with a low relative abundance of bifidobacteria is selected from enteropathogenic infections, impaired gut-barrier function, type-2 diabetes, gut brain disorders, allergies, asthma, and/or inflammatory bowel conditions.

3. The method of claim 1, wherein the non-infant human subject suffers from or is at risk of developing enteropathogenic infections, impaired gut-barrier function, type-2 diabetes, gut brain disorders, allergies, asthma, and/or inflammatory bowel conditions.

4. The method of claim 1 wherein the non-infant human subject is an adult human subject of over 18 years of age.

5. The method of claim 1, wherein the weight ratio GOS:2'-FL is in the range of 1:8-8:1.

6. The method of claim 1, wherein daily dosage of GOS plus 2'-FL that is administered to said non-infant human subject is in the range of 0.5-30 g.

7. The method of claim 1, wherein said nutritional composition has the form of a beverage, ice cream, bar, snack, bakery product, sweet, candy, pasta, or food supplement.

8. A method of increasing the relative abundance of bifidobacteria in the gastro intestinal tract of a non-infant human subject, the method comprising administering to the non-infant human subject an effective amount of a nutritional composition comprising galacto-oligosaccharide (GOS) and 2'-Fucosyllactose (2'-FL) in a GOS: 2'-FL weight ratio of 1:9-9:1.

9. The method of claim 8 wherein the weight ratio GOS:2'-FL is in the range of 1:8-8:1.

10. The method of claim 8 wherein the non-infant human subject is an adult of over 18 years of age.

11. The method of claim 1, wherein the bifidobacteria comprises *Bifidobacterium adolescentis* and/or *Bifidobacterium longum*.

12. The method of claim 2, wherein the gut brain disorders comprise stress, anxiety, and/or depression, the allergies comprise atopic dermatitis, and the inflammatory bowel conditions comprise inflammatory bowel disease (IBD).

13. The method of claim 3, wherein the gut brain disorders comprise stress, anxiety, and/or depression, the allergies comprise atopic dermatitis, and the inflammatory bowel conditions comprise inflammatory bowel disease (IBD).

14. The method of claim 4, wherein the non-infant human subject is an adult human subject of over 40 years of age.

15. The method of claim 5, wherein the weight ratio GOS:2'-FL is in the range of 1:7-7:1.

16. The method of claim 6, wherein daily dosage of GOS plus 2'-FL that is administered to said non-infant human subject is in the range of 0.5-20 g.

17. The method of claim 8, wherein the bifidobacteria comprises *Bifidobacterium adolescentis* and/or *Bifidobacterium longum*.

18. The method of claim 9, wherein the weight ratio GOS:2'-FL is in the range of 1:7-7:1.

19. The method of claim 10, wherein the non-infant human subject is an adult of over 40 years of age.

* * * * *